United States Patent [19]

Karger et al.

[11] Patent Number: 4,940,883

[45] Date of Patent: Jul. 10, 1990

[54] WINDOW BURNER FOR POLYMER COATED CAPILLARY COLUMNS

[75] Inventors: Barry L. Karger, Newton; Robert J. Nelson, Boston, both of Mass.

[73] Assignee: Northeastern University, Boston, Mass.

[21] Appl. No.: 342,989

[22] Filed: Apr. 24, 1989

[51] Int. Cl.$^5$ ............................................. H05B 3/02
[52] U.S. Cl. ..................................... 219/200; 219/221
[58] Field of Search ............... 219/200, 201, 221, 227, 219/231, 242, 263, 270; 81/9.51; 83/15, 16, 170, 171

[56] References Cited

U.S. PATENT DOCUMENTS

| | | | |
|---|---|---|---|
| 2,192,096 | 2/1940 | Watts | 81/9.51 |
| 2,396,594 | 3/1946 | Moore | 219/200 |
| 3,041,439 | 6/1962 | Sisk | 219/221 |
| 3,985,996 | 10/1976 | Fischer | 219/221 |

FOREIGN PATENT DOCUMENTS

| | | | |
|---|---|---|---|
| 1050415 | 2/1959 | Fed. Rep. of Germany | 81/9.51 |
| 799008 | 7/1958 | United Kingdom | 219/221 |

Primary Examiner—Teresa J. Walberg
Attorney, Agent, or Firm—Weingarten, Schurgin, Gagnebin & Hayes

[57] ABSTRACT

A window burner for creating windows by selective removal of polymer type coatings from capillary columns and very small diameter tubes. The burner includes an electric circuit which provides a predetermined, controlled current from a standard 120 or 220 volt AC outlet. The predetermined, controlled current electrically heats a resistive wire for a predetermined period of time. The resistive wire may have a predetermined configuration to facilitate mounting of the capillary column for selective burning. The size of the resistive wire and the predetermined period of time during which the predetermined, controlled current is provided thereto are factors determining the size of the window formed by selectively burning off the polymer coating.

16 Claims, 2 Drawing Sheets

WINDOW BURNER FOR POLYMER COATED CAPILLARY COLUMNS

RELATED APPLICATION

This application is related to U.S. Pat. No. 4,898,658 entitled INTEGRATED TEMPERATURE CONTROL/ALIGNMENT SYSTEM FOR HIGH PERFORMANCE CAPILLARY ELECTROPHORETIC APPARATUS, issued Feb. 6, 1990.

FIELD OF THE INVENTION

This invention relates generally to devices utilizing small-diameter tubes having an external polymer coating such as high performance capillary electrophoretic apparatus, and more particularly, to a window burner for selectively removing the polymer coating from polymer-coated capillary columns to provide sensing-/measurement windows therein.

BACKGROUND OF THE INVENTION

Capillary electrophoresis is a technique for analyzing and/or purifying a wide variety of biochemical substances or analytes such as proteins, nucleic acids, carbohydrates, hormones and vitamins. The basic capillary electrophoretic apparatus consists of a capillary column having the ends thereof positioned in reservoirs containing electrodes. A conducting liquid or buffer solution disposed in the reservoirs and the capillary column comprises the electrophoretic conductive circuit. The analyte is injected into the appropriate end of the capillary column and a voltage applied across the electrodes. The applied voltage causes the analyte to migrate electrophoretically through the capillary column past a prepositioned on-column detection device to generate an electropherogram, a graphical representation of the analyte.

The capillary columns utilized in electrophoretic systems are thin walled, hollow tubes preferably formed from a low specific heat, non-electrically conducting material such as fused silica. Capillary columns for use in electrophoretic systems typically have a length in the range of 10 to 100 cm, an internal diameter in the range of 25 to 200 microns, and an outer diameter in the range of 125 to 350 microns, depending upon the I.D. of the capillary column.

A quartz based fused silica capillary column having the above-disclosed dimensions, however, is relatively fragile and susceptible to fracture or breakage due to handling and/or externally applied forces. Therefore, the mechanical strength and flexibility of capillary columns for electrophoretic systems are generally enhanced by applying an external protective coating of a polymer such as polyimide to the capillary columns.

The polymer coating, however, would interfere with the operation of the on-column detection device inasmuch as the polymer coating inhibits the measurement or sensing of the electromigrating analyte during passage through the interior of the capillary column. Therefore, as illustrated in FIG. 1, the polymer coating of a capillary column CC must be modified to include detection "windows W". It is to be understood that "windows" is used in a generic sense to include not only a window W formed by selectively removing a 360 degree band of polymer coating as shown in FIG. 1 but also the selective removal of the polymer coating to form partial windows. Such modification includes the selective removal of the polymer coating at a predetermined position on the capillary column.

While the Background has been set forth in terms of capillary columns used in electrophoretic apparatus, it will be appreciated that the problems described in the preceding paragraphs are inherent in other applications such as open-tube liquid chromatography and supercritical fluid chromatography. There are many applications wherein sensing/measurement or other type windows must be formed in small-diameter tubes or columns which are mechanically reinforced by means of an external polymer-type coating by selective removal of the polymer-type coating. It is therefore to be understood that the window burner of the present invention is not limited to polymer-coated capillary columns utilized in electrophoretic apparatus.

Several methods are known for removing the polymer coating on quartz based fused silica capillary columns. A razor blade may be used to scrape the polymer coating from the capillary column. This method is disadvantageous in that the column is extremely susceptible to fracture or breakage. The slightest etching of the glass during removal of the polymer coating reduces the mechanical strength of the column. In addition, fracture or breakage may be incurred due to the increased handling or the force applied through the razor blade. In addition, this method is extremely unreliable in producing windows of consistent dimension.

In addition to retention of mechanical integrity, very precise uniformity of dimension must be maintained among windows produced by removing the polymer coating from the capillary columns. This precise uniformity is not attainable through the use of razor blades.

Another method involves the application of an open flame to burn the polymer coating from the capillary column. This method, however, has several drawbacks. A flame device requires a gas supply and a very small needle tip to develop an appropriate flame. Setting up flame devices for operation is a time consuming and labor intensive operation. In addition, the flame and/or gas supply are potential sources of fire or explosion. Flame devices typically generate more heat than is required to remove the polymer coating, oft times resulting in bent, melted or useless capillary columns. Flame devices generally do not provide precise uniformity of dimension in the windows formed, and many such devices create windows so large that the column becomes very fragile.

High voltage arc devices can be used to create windows in capillary columns. These devices, however, do not provide precise uniformity of dimension in the windows created due to the difficulty in controlling the arc generated. In addition, high voltage arc devices tend to be prohibitively expensive for the task, costing several thousands of dollars apiece.

SUMMARY OF THE INVENTION

To overcome the inherent limitations of the prior art, an inexpensive window burner for creating uniform and reproducible windows in polymer coated capillary columns is disclosed. The window burner of the present invention permits a window to be precisely created in less than 10 seconds. The window burner of the present invention also provides controlled reproducibility, thereby providing precise uniformity of dimension in the windows created. Further, the window burner provides controlled heating via a controlled current to selectively remove the polymer coating, thereby minimizing damage to the capillary column. The window burner is easy to set up and provides for safe operation.

The window burner includes a housing, an activation switch, circuit means and a resistively heated wire electrically connected to the circuit means. The circuit means is adapted to interface with a conventional power source such as a 120 or 220 volt AC wall outlet. The circuit means is energized by the activation switch and transforms the input voltage into a predetermined, controlled current which flows through the resistively heated wire for a predetermined period of time to selectively burn off a predetermined portion of the polymer coating of the capillary column.

The resistively heated wire has a configuration such that the capillary column is in contact therewith. The configuration of the resistive wire may include one or more well portions into which one or more capillary columns may be mounted for selective burning. In another embodiment, the configuration of the wire may be straight and one or more capillary columns rested in contact with the wire for selective burning. In yet another embodiment a pair of spaced apart contact wires may be utilized with the capillary column interposed in contact therebetween.

The gauge of the resistive wire, in conjunction with the predetermined period of time during which the predetermined, controlled current is provided, determines the amount of polymer coating that is selectively burned off of the capillary column. The predetermined, controlled current flowing through the resistively heated wire electrically heats the wire to a predetermined temperature to selectively burn the polymer coating from the capillary column to form a window therein of precise dimension. Reproducibility among windows formed by use of the window burner of the present invention is ensured by the controlled operating conditions thereof.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF PREFERRED EMBODIMENTS

Figure 1:
FIG. 1 illustrates a fused capillary column having a window formed therein.
Figure 2:
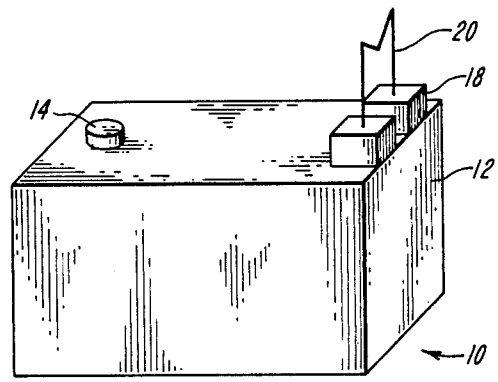
FIG. 2 is a perspective view of a window burner for polymer coated capillary columns according to the present invention.

Referring now to the drawings wherein like numerals represent corresponding or similar elements throughout the several views, there is shown in FIG. 2 an exemplary embodiment of a window burner 10 for polymer coated capillary columns according to the present invention. The window burner 10 includes a housing 12, an external activation switch 14, an internal circuit means 16 (FIG. 3) for generating a predetermined controlled current, mechanical fittings 18, 18, and an external resistively heated wire 20 configured for mounting in the mechanical fittings 18, 18. The mechanical fittings 18, 18 are preferably formed from a thermally insulative material to preclude injuries from inadvertent contact therewith when the wire 20 is heated.

Figure 3:
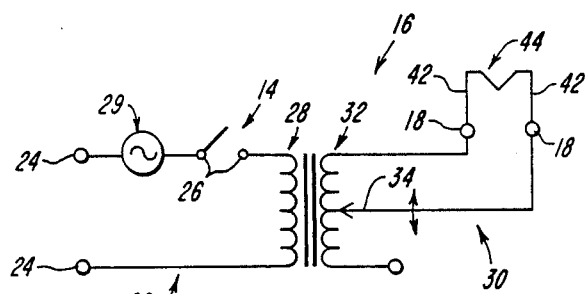
FIG. 3 is schematic view of an exemplary circuit for the window burner of the present invention.

The circuit means 16 which is disposed within the housing 12 is exemplarily illustrated in FIG. 3. The circuit means 16 is a transformer which includes primary and secondary circuits 22, 30, respectively, for generating the predetermined controlled current which flows through the resistively heated wire 20. The primary circuit 22 includes a connection means 24 such as a two or three prong plug for connecting the primary circuit 22 to a conventional 120 or 220 volt AC wall outlet, connection points 26 interfacing with the external activation switch 14 to permit opening and closing of the primary circuit 22 and a primary transformer coil 28. The primary circuit 22 may also include a fuse 29 to protect the primary circuit 22 against external voltage surges.

The secondary circuit 30 includes a secondary transformer coil 32, one side of which is electrically connected to one mechanical fitting 18. The secondary transformer coil 32 may be center tapped or may be adjustably tapped. The adjustable tap 34 illustrated in FIG. 3 is electrically interconnected to the other mechanical fitting 18. It will be appreciated that for embodiments having a center tapped secondary transformer coil 32, the center tap would be electrically interconnected to the other mechanical fitting 18.

The secondary transformer coil 32 permits a predetermined, controlled current 36 to be generated in the secondary circuit 30. For example, in an embodiment similar to that illustrated in FIG. 3, with the plug 24 connected to 120 volts AC, the center tap or the adjustable tap 34 is positioned so that a 5 volt potential is developed across the secondary transformer coil 32, thereby causing a predetermined controlled current 36 of 5 amperes to flow through the secondary circuit 30 and the resistively heated wire 20.

The resistively heated wire 20 may have a configuration as generally shown in FIGS. 2 and 3. The resistively heated wire 20 has first and second spaced apart legs 42, 42 which are configured for connection with the mechanical fittings 18, 18 and an intermediate portion 44 electrically interconnecting the legs 42, 42. The intermediate portion 44 is formed to include a well configuration for supporting a capillary column CC of predetermined external diameter.

Alternatively, the intermediate portion 44 may have a straight configuration. In this embodiment, the capillary column CC is mounted in contact with the resistive wire 20 by resting the capillary column CC on the straight intermediate portion.

The resistively heated wire 20 exemplarily illustrated in FIGS. 2 and 3 generally has a length of about 3 inches. The wire 20 is formed from a conductive material such as 30 gauge nichrome which has a nominal resistance of about 1 ohm per foot. The gauge size of the heated wire 20 is one factor which determines the dimension of the window W which is formed in the capillary column CC by the window burner 10.

The activation switch 14 may be one of several types. The activation switch 14 may be a dual-pole switch having ON and OFF positions. Alternatively, the activation switch 14 may be a pushbutton which energizes the circuit means 16 as long as the button is depressed. Or, the activation switch 14 may be a timer switch which energizes the circuit means 16 for a predetermined period of time.

To operate the window burner 10 of the present invention, the plug 24 is connected to a convenient wall outlet. An appropriately sized and configured wire 20 is connected to the mechanical fittings 18, 18. A capillary column CC is supported in contact with the intermediate portion 44 of the wire 20. The activation switch 14 is operated to cause a predetermined, controlled current 36 to flow through the heated wire 20 for a predetermined period of time to heat the wire 20 to a predetermined temperature.

The heat generated by the wire 20 causes the polymer coating of the portion of the capillary column CC supported in the well 44 to be selectively burned off to form the window W. Since the gauge of the wire 20, in combination with predetermined period of time during which the predetermined, controlled current 36 is flowing through the wire 20, determines the dimension of the window W, windows W having precise uniformity of dimension may be formed in any number of capillary columns.

Figure 4:
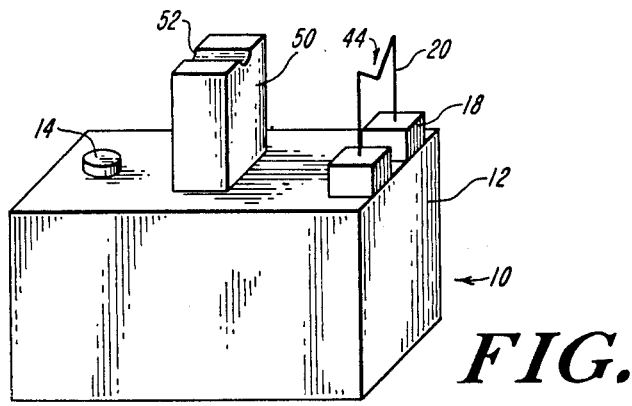
FIGS. 4, 5A, and 5B are other embodiments of a window burner according to the present invention.

Another embodiment of a window burner 10 is illustrated in FIG. 4, and includes, in addition to the elements described hereinabove, a capillary support 50. The support 50 is spaced apart from the resistively heated wire 20 and is configured with a well 52 to support the capillary column CC, in combination with the intermediate portion 44 of the wire 20, in a position for selective burning thereof. The support 50 stabilizes the capillary column CC during the selective burning operation and facilitates ease of operation of the window burner 10 of the present invention.

Figure 5A:
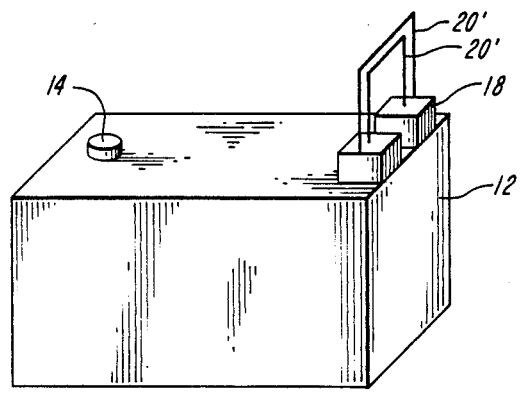
Figure 5B:
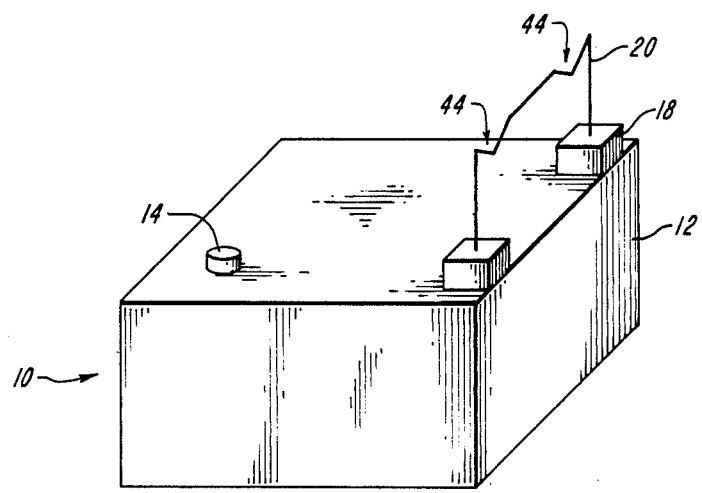

Other embodiments of the window burner 10 are possible. For example, the wire 20 of the window burner 10 may have multiple wells formed in the intermediate portion 44 thereof as shown in FIG. 5B, thereby facilitating the formation of windows W in multiple capillary columns CC during a single selective burning operation. Preferably, this embodiment would include a capillary support 50' having multiple wells 52 for supporting the multiple capillary columns CC.

In another embodiment, the capillary support 50' would be used in combination with the aforedescribed resistive wire having a straight intermediate portion 44 to facilitate the formation of windows W in multiple capillary columns CC during a single selective burning operation. In another embodiment, shown in FIG. 5A, a pair of spaced apart wires 20', each having the predetermined, controlled current 36 flowing therethrough for the predetermined period of time, would be utilized for selective burning of the capillary column CC which would be interposed in contact between the pair of spaced apart wires 20'.

A measuring means such as a ruler or caliper may be utilized in combination with the resistive wire to ensure that the window W is selectively burned in the capillary column CC a predetermined distance from one end thereof for applications wherein the positioning of the window W is a critical factor. For example, in some high performance electrophoretic apparatus the window W needs to be positioned about 15 cm from one end of the capillary column. The positioning of such a window W generally depends on the detection system used for sensing/measurement.

A variety of modifications and variations of the present invention are possible in light of the above teachings. It is therefore to be understood that within the scope of the appended claims, the present invention may be practiced otherwise than as specifically described hereinabove.

What is claimed is:

1. A window burner for creating a window of uniform dimension in a polymer coated capillary column by selective removal of a predetermined portion of the polymer coating thereof, comprising:

circuit means for generating a predetermined, controlled current for a predetermined period of time; and resistive wire means electrically coupled to said circuit means and configured for mounting of the polymer coated capillary column for selectively burning off the predetermined portion of the polymer coating of the mounted capillary column to create the window of uniform dimension therein, said resistive wire means having a predetermined gauge to provide the uniformity of dimension among windows created by said window burner; and wherein said predetermined, controlled current flows through said resistive wire means of said predetermined gauge for said predetermined period of time to heat said resistive wire means to a predetermined temperature to selectively burn off the predetermined portion of the polymer coating of the mounted capillary column; and further wherein said predetermined gauge of said wire resistive means and said predetermined, controlled current flowing for said predetermined period of time in combination define the predetermined portion of the polymer coating selectively burned off of the mounted capillary column wherein said window burner reproducibly creates windows of uniform dimension.

2. The window burner of claim 1 wherein said circuit means further comprises primary and secondary circuits;

said primary circuit including means for connecting said primary circuit to an external power source, and a primary transformer coil electrically connected to said connecting means, and;

said secondary circuit including a secondary transformer coil electromagnetically coupled to said first transformer coil, and means for electrically coupling said secondary transformer coil to said resistive wire means; and wherein activation of said primary circuit by the external power source causes said predetermined, controlled current to be generated by said secondary transformer coil for said predetermined period of time and to flow through said resistive wire means.

3. The window burner of claim 2 further comprising:

activation switch means coupled to said primary circuit for causing said primary circuit to be energized by the external power source for said predetermined period of time, thereby generating said predetermined, controlled current in said secondary circuit.

4. The window burner of claim 3 wherein said activation switch means is a push button which causes said primary circuit to be energized by the external power source when in a depressed condition for said predetermined period of time.

5. The window burner of claim 3 wherein said activation switch means is a timer switch which energizes said primary circuit or said predetermined period of time when momentarily depressed.

6. The window burner of claim 1 wherein said resistive wire means is a conductive wire having a predetermined length and said predetermined gauge.

7. The window burner of claim 6 wherein said conductive wire comprises:
   first and second spaced apart legs configured for electrical coupling to said circuit means; and
   an intermediate portion integrally joining said first and second spaced apart legs, said intermediate portion having a configuration for mounting the capillary column to selectively burn off the predetermined portion of the polymer coating of the mounted capillary column to create the window of uniform dimension therein.

8. The window burner of claim 7 wherein said intermediate portion has at least one well formed therein to receive the capillary column for selectively burning off the predetermined portion of the polymer coating thereof to create the window of uniform dimension therein.

9. The window burner of claim 1 wherein said resistive wire means comprises first and second conductive wires spaced apart from one another so that the capillary column may be interposed there between to selectively burn off the predetermined portion of the polymer coating thereof, each said first and second conductive wires having a predetermined length and said predetermined gauge.

10. The window burner of claim 1 further comprising:
    capillary support means spaced apart from said resistive wire means for supporting the capillary column in combination with said resistive wire means in a position for selective burning off of the predetermined portion of the polymer coating of the capillary column.

11. The window burner of claim 1 further comprising:
    means for housing said circuit means, said housing means including mechanical fitting means for electrically coupling said resistive wire means to said circuit means disposed in said housing means.

12. The window burner of claim 11 wherein said mechanical fitting means includes first and second thermally insulative members depending outwardly from said housing means, said thermally insulative members configured to mechanically receive said resistive wire means to couple said resistive wire means to said circuit means.

13. A window burner for creating windows of uniform dimension in polymer coated capillary columns by selective removal of predetermined portions of the polymer coatings thereof, comprising:
    circuit means for generating a predetermined, controlled current for a predetermined period of time; and
    resistive wire means electrically coupled to said circuit means and configured for mounting at least two polymer coated capillary columns for selectively burning off the predetermined portions of the polymer coatings there to create the windows of uniform dimension therein, said resistive wire means having a predetermined gauge to provide the uniformity of dimension among the windows created by said window burner; and wherein
    said predetermined, controlled current flows through said resistive wire means of said predetermined gauge for said predetermined period of time to heat said resistive wire means to a predetermined temperature to selectively burn off the predetermined portions of the polymer coatings of the at least two mounted capillary columns; and further wherein
    said predetermined gauge of said wire resistive means and said predetermined, controlled current flowing for said predetermined period of time in combination define the predetermined portions of the polymer coatings selectively burned off of the at least two mounted capillary columns wherein said window burner reproducibly creates windows of uniform dimension.

14. The window burner of claim 13 further comprising:
    capillary support means spaced apart from said resistive wire means for supporting the at least two capillary columns in combination with said resistive wire means in position for selective burning off the predetermined portions of the polymer coatings of the at least two capillary columns.

15. The window burner of claim 13 wherein said resistive wire means comprises first and second conductive wires spaced apart from one another so that the at least two capillary columns may be interposed there between to selectively burn off the predetermined portions of the polymer coatings thereof, each said first and second conductive wires having a predetermined length and said predetermined gauge.

16. The window burner of claim 13 wherein said resistive wire means comprises a conductive wire having a predetermined length and said predetermined gauge, said conductive wire having first and second spaced apart legs configured for electrical coupling to said circuit means; and
    an intermediate portion integrally formed with said first and second spaced apart legs, said intermediate portion including at least first and second well portions configured to receive the at least two capillary columns, each said at least first and second well portions having a configuration for mounting one of the at least two capillary columns to selectively burn off the predetermined portions of the polymer coatings of the at least two mounted capillary columns to create the windows of uniform dimension therein.

* * * * *

UNITED STATES PATENT AND TRADEMARK OFFICE
CERTIFICATE OF CORRECTION

PATENT NO. : 4,940,883
DATED : July 10, 1990
INVENTOR(S) : Barry L. Karger

It is certified that error appears in the above-identified patent and that said Letters Patent is hereby corrected as shown below:

Column 6, line 67, "or" should read --for--.

Column 8, line 5, "there" should read --thereof--.

Signed and Sealed this

Fourth Day of August, 1992

Attest:

DOUGLAS B. COMER

*Attesting Officer*  *Acting Commissioner of Patents and Trademarks*